US00PP11696P

United States Patent [19]

Heffner

[11] Patent Number: Plant 11,696

[45] Date of Patent: Dec. 19, 2000

[54] VARIETY OF PETUNIA NAMED 'TRUMPET RED'

[75] Inventor: Mike Heffner, Lompoc, Calif.

[73] Assignee: John Bodger and Sons Company, South El Monte, Calif.

[21] Appl. No.: 09/169,700

[22] Filed: Oct. 9, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 10,234 2/1998 Adolph ..... Plt./356

*Primary Examiner*—Bruce R. Campell
*Assistant Examiner*—Wendy A Baker
*Attorney, Agent, or Firm*—Fulwider Patton Lee & Utecht, LLP

[57] ABSTRACT

The claimed cultivar brings a new color to the Trumpet series of Petunias and is characterized by a red colored flower accented at its throat with a lighter red color exhibiting darker red veining. As with all Trumpet Petunias, this cultivar exhibits early flowering with superior branching so that the plant may also be used in a hanging pot.

1 Drawing Sheet

BACKGROUND OF THE NEW PLANT

The present invention relates to a new and distinct variety of Petunia known by the name 'Trumpet Red' (Bodger No. 7P3430-2). The new variety was discovered in a selective breeding program by Mike Heffner at Bodger Seeds, Ltd., Lompoc, Calif. The new variety is a selection from the crossing of inventor's proprietary Petunia selection Bodger No. 7P968-6 (unpatented), the female parent, which is a seedling with spreading decumbent habit and small red colored flowers, with inventor's proprietary Petunia selection Bodger No. 7P1143-9 (unpatented), the male parent, which a is seedling with spreading habit and large red flowers. The male parent is weaker than and is distinguishable from 'Trumpet Red' by its shorter stems, 30 cm as contrasted with 46 cm. Additionally, the male parent has smaller flowers. The female parent is distinguished by its small red flowers as contrasted with the large flowers of 'Trumpet Red'.

This new variety is the result of a breeding program whose objective was to develop new vegetatively propagated petunias with a spreading cascading habit, large flowers and with a color range not presently available as a cutting product. The variety originated from a cross between two proprietary seedling selections taken from the existing breeding program. The progeny from this cross was grown out during the summer of 1997 and a number of single plants were selected as possible new varieties and propagated vegetatively. The cuttings were trialed and evaluated during winter and summer of 1998 at which time it was determined that this particular line, established from one single plant, was distinguishable and unique.

The new cultivar was first asexually reproduced by terminal vegetative cuttings at Bodger Seeds, Ltd., Lompoc, Calif. and has been repeatedly asexually reproduced by cuttings at Bodger Seeds Ltd., at Lompoc Calif. It has been found to be stable and true to type through successive propagations.

The new cultivar was grown in a glass greenhouse in Lompoc, Calif., using full light, 60° Fahrenheit night temperature, 77° Fahrenheit day temperature, and grown in soil having a temperature of 80° Fahrenheit. The claimed plant was grown from a terminal vegetative cutting, and exhibited an eight to ten weeks response time from an unrooted cutting to a 25 cm flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Bodger Seeds Ltd., in Lompoc, Calif. The plant histories were taken on rooted cuttings believed to have been potted in a 25 cm pot, under full light in the greenhouse, and color readings were taken in day light using The Royal Horticultural Society of London Colour Chart.

THE PLANT

Classification:
- *Botanical.*—*Petunia×hybrida Hort.*
- *Commercial.*—'Trumpet Red' petunia.

Form: Indeterminate with spreading and decumbent habit. When planted in a hanging pot the stems hang down.
- *Height.*—14 cm above the top of pot.
- *Spreading area of plant.*—92 cm in diameter.

Foliage: Freely branching.

Leaves: Leaves are simple, opposite; pinnate venation; foliage viscid; leaves horizontal to stem; numerous shoots at internodes.
- *Size.*—5.4 cm length when fully expanded. 3.1 cm width when fully expanded. 1.5 mm thickness.
- *Shape.*—Elliptic.
- *Margin.*—Entire.
- *Texture.*—Sparsely pubescent.
- *Color.*—Upper: Green Group 137A. Lower: Yellow-Green Group 146B.
- *Apex.*—Acute.
- *Base.*—Obtuse.

Stem:
- *General.*—Hanging; Spreading to a length of 46 cm.
- *Color.*—Yellow-Green Group 144A.
- *Internode length.*—4.8 cm.
- *Diameter.*—0.3 cm.
- *Anthocyanin pigmentation.*—Absent.
- *Texture.*—Pubescent.

INFLORESCENCE

Young flower:
*Diameter.*—5.9 cm.
*Length.*—5.0 cm.
*Color.*—Inside: Petals Red Group 45A; throat light Red-Group 49C with veins in throat dark Greyed-Purple Group 184C. Outside: Greyed-Red Group 180C with slight veins in Green Group 152B.

Mature flower:
*Diameter.*—7.4 cm.
*Length.*—5.5 cm.
*Color.*—Inside: Petals Red Group 50A; throat light Red Group 50D with veins in throat dark Greyed-Purple Group 184C. Outside: Greyed-Red Group 180C with slight veins in Yellow-Green Group 152B.

Open florets:
*Form.*—Single funnelform flowers; calyx five parted, petals united into flower tube; petal apex rounded to broadly acuminate.
*Texture and appearance.*—Smooth on inside, pubescent on outside, presenting large red flowers.

Pedicel:
*Length.*—2.4 cm.
*Thickness.*—0.3 cm.
*Texture.*—Pubescent.

Sepals:
*Quantity.*—5.
*Length.*—1.6 cm.
*Width.*—0.4 cm.
*Shape.*—Elliptic.
*Color.*—Inside: Green Group 137A. Outside: Green Group 137C.
*Apex.*—Obtuse.
*Margin.*—Entire.
*Texture.*—Pubescent.

Persistence:
*Disease resistance.*—No known special disease resistance compared with other Petunias.

REPRODUCTIVE ORGANS

Stamens:
*Number.*—5 normal stamens.
*Anthers.*—2 level with stigma; 3 below stigma; Yellow-white.
*Filaments.*—White.

Pistils:
*Number.*—1 normal.
*Stigma.*—Green.
*Style.*—Yellow-green.

Ovaries: Superior.

GENERAL CHARACTERISTICS

'Trumpet Red' brings a new and distinct color to the Trumpet Series of Petunias which is a group of varieties that are early flowering and very floriferous having large blooms with numerous branching at internodes over a lighter green foliage. At maturity 'Trumpet Red' has approximately 150–200 open blooms per 25 cm pot. 'Trumpet Red' presents a large red colored flower exhibiting a lighter red throat having dark red veining in the throat. The flowers open above the foliage and face outwards and have no fragrance. The variety shows normal fertility and seed set.

I claim:

1. A new and distinct variety of Petunia plant, substantially as shown and described.

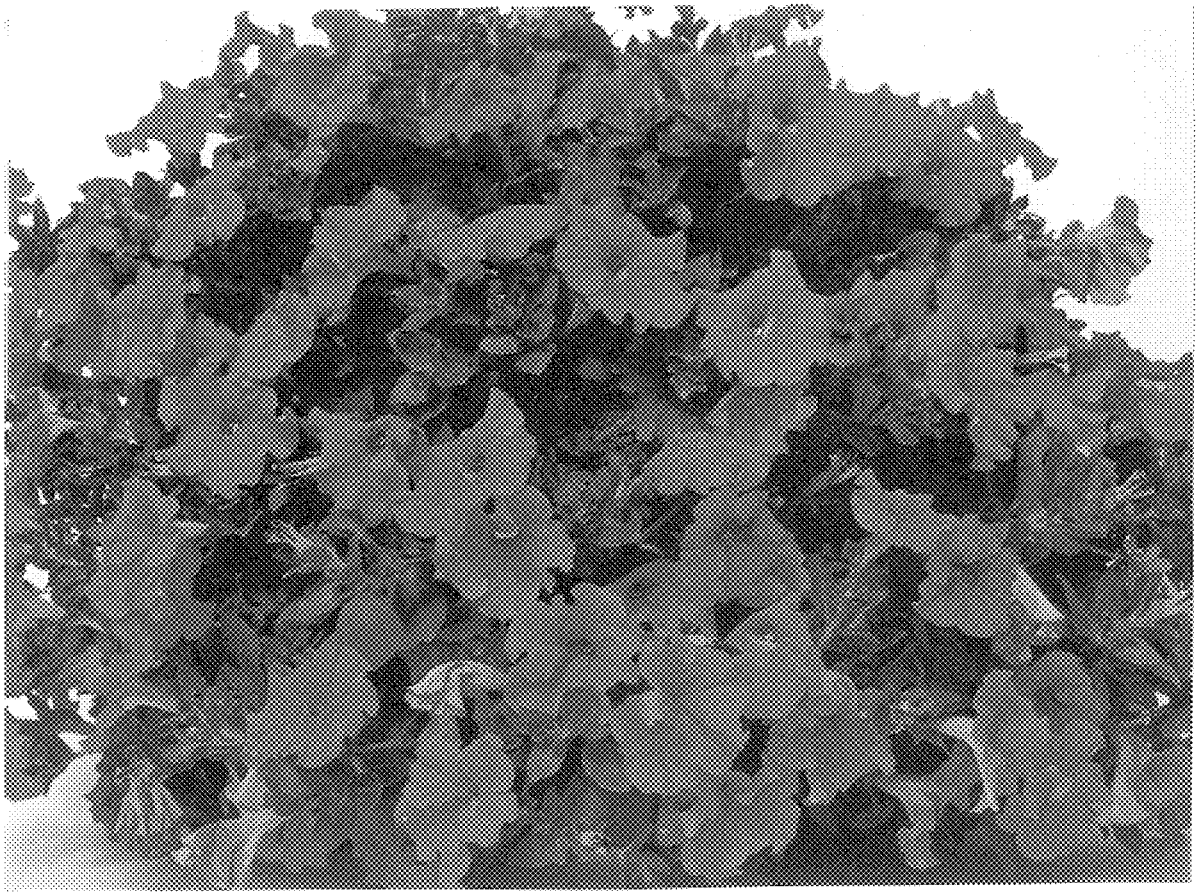

* * * * *